(12) United States Patent
Hayase et al.

(10) Patent No.: US 6,451,000 B1
(45) Date of Patent: *Sep. 17, 2002

(54) DISPOSABLE DIAPER

(75) Inventors: Toru Hayase; Harumitsu Toyoda; Haruko Kawaguchi, all of Tochigi-ken (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/906,924

(22) Filed: Aug. 5, 1997

Related U.S. Application Data

(63) Continuation of application No. 08/523,891, filed on Sep. 6, 1995, now abandoned, which is a continuation of application No. 08/220,697, filed on Mar. 31, 1994, now abandoned.

(30) Foreign Application Priority Data

Apr. 5, 1993 (JP) .............................. 5-016721
Apr. 19, 1993 (JP) .............................. 5-019939

(51) Int. Cl.⁷ ............................ A61F 13/15; A61F 13/20
(52) U.S. Cl. ............................ 604/385.13; 604/385.27; 604/385.29; 604/385.3; 604/396
(58) Field of Search .................... 604/385.1, 385.2, 604/389–396, 386, 385.19

(56) References Cited

U.S. PATENT DOCUMENTS

| | | | |
|---|---|---|---|
| 3,840,013 A | * 10/1974 | Mesek et al. | 604/396 |
| 3,848,594 A | * 11/1974 | Buell | |
| 3,874,386 A | * 4/1975 | Kozak | 604/390 |
| 3,920,019 A | 11/1975 | Schaar | |
| 3,927,674 A | * 12/1975 | Schaar | 604/385.1 |
| 3,930,502 A | 1/1976 | Tritsch | |

(List continued on next page.)

FOREIGN PATENT DOCUMENTS

| | | | | |
|---|---|---|---|---|
| DE | 3419621 | | 5/1984 | |
| DE | 4033850 A1 | | 4/1992 | |
| EP | 0321234 A1 | | 6/1989 | |
| EP | 0487921 | * | 6/1992 | 604/385.2 |
| GB | 2129689 A | | 5/1984 | |
| JP | 58-22908 | * | 2/1983 | |
| JP | 61-207605 | | 9/1986 | |
| JP | 63-74119 | | 5/1988 | |
| JP | 2-69906 | | 5/1990 | |
| JP | 2-139628 | | 11/1990 | |
| JP | 0318831 | | 1/1991 | |
| JP | 3-16920 | | 2/1991 | |
| JP | 3-16923 | | 2/1991 | |
| JP | 3176082 | * | 7/1991 | 604/394 |
| JP | 4-44920 | | 4/1992 | |
| JP | 4117618 | | 10/1992 | |
| WO | 9409736 | | 5/1994 | |

OTHER PUBLICATIONS

"How to dispose the pants after use", Ekubo Club Magazine, 7 pages, (no date).

Primary Examiner—John G. Weiss
Assistant Examiner—K. M. Reichle
(74) Attorney, Agent, or Firm—Birch, Stewart Kolasch & Birch, LLP

(57) ABSTRACT

A short-type disposable diaper including a liquid permeable topsheet, a liquid impermeable backsheet, and an absorber interposed between the topsheet and the backsheet, front and rear waist portions being connected together at opposite sides thereof, respectively, the improvement including a tape fastener adapted to fasten the diaper when the diaper is to be discarded, the tape fastener being disposed at a central outer surface section of the backsheet and extending in a longitudinal direction of the backsheet.

3 Claims, 11 Drawing Sheets

U.S. PATENT DOCUMENTS

| | | |
|---|---|---|
| 4,047,529 A | 9/1977 | Karami |
| 4,127,132 A * | 11/1978 | Karami .................... 604/390 |
| 4,205,679 A * | 6/1980 | Repke et al. ............... 604/394 |
| 4,641,381 A | 2/1987 | Heran et al. |
| 4,643,729 A * | 2/1987 | Laplanche ................. 604/396 |
| 4,646,362 A | 3/1987 | Heran et al. |
| 4,670,012 A | 6/1987 | Johnson |
| 4,738,678 A * | 4/1988 | Paulis ..................... 604/385.1 |
| 4,834,820 A | 5/1989 | Kondo et al. |
| 4,869,724 A * | 9/1989 | Scripps ..................... 604/391 |
| 4,940,464 A | 7/1990 | Van Gompel et al. |
| 4,968,311 A * | 11/1990 | Chickering et al. ....... 604/385.1 |
| 5,071,414 A * | 12/1991 | Elliott .................... 604/385.1 |
| 5,141,505 A * | 8/1992 | Barrett .................... 604/396 |
| 5,176,671 A * | 1/1993 | Roessler et al. ............ 604/391 |
| 5,182,156 A | 1/1993 | Pape et al. |
| 5,288,546 A * | 2/1994 | Roessler et al. ............ 604/391 |
| 5,370,634 A * | 12/1994 | Ando et al. ............... 604/385.1 |
| 6,063,066 A * | 5/2000 | Inoue et al. ................ 604/389 |

* cited by examiner

DISPOSABLE DIAPER

This application is a X continuation, of application Ser. No. 08/523,891, filed on Sep. 6, 1995, now abandoned, which was a continuation of application Ser. No. 08/220,697, filed on Mar. 31, 1994, now abandoned.

BACKGROUND OF THE INVENTION

1. Field of the Invention

This invention relates to an infant's diaper, toilet training shorts, and a disposable diaper for the use of an adult or an incontinent person, and particularly to a shorts type disposable diaper.

2. Description of the Prior Art

Conventional disposable diapers are mostly of the flat type, in which a flat diaper body is placed against the wearer and thereafter fastened by a tape fastener. For discarding such flat type diapers after use, the diapers are rolled up in such a manner as to contain discharged materials and then fastened by the tape fastener.

Recently, there has been developed a so-called shorts type diaper in which side portions thereof are preliminarily fixedly connected without using any tape fastener. Various kinds of shorts type diapers of this type are proposed, including one in which gathers are provided at a waist portion and leg portions, for example. (Japanese Laid Open Patent Application Nos. Sho 58-115106, Sho 58-115107, Sho 62-231005, etc.) These shorts type diapers can all be worn by the wearer in a standing position as in the case with the normal undergarments. They are intended to be used not only by infants as diapers, but also by month-wise aged babies (babies of about eight to twelve months old) as a toilet training wear, or by incontinent persons and adults as a diaper.

However, since those shorts type diapers are not provided with a tape fastener, the diapers rolled up for discarding cannot be fastened and are therefore difficult to be discarded. If the discharged materials contained in the diapers are soft feces or loose bowels having high fluidity, they are sometimes exposed to the outside of the diaper. This is problematical also from a sanitary aspect when the diapers are to be discarded.

Although the conventional shorts type disposable diapers have an advantage such as having a flexible fitness to an active older baby, they have a disadvantage such that they are difficult to well fit to wearers of all sizes within the limit of the expansibility of the gathers (that is, only with the aid of the expansibility of the gathers). As a result, the wearer's skin is damaged by the elasticity of the gathers and the diaper slips down to permit the discharged materials in the diaper to leak outside.

Furthermore, the conventional shorts type disposable diaper has the additional problems in that the discharged materials in the diaper, in use, cannot be seen from outside, at least one side of the diaper must be torn off in order to handle the discharged materials, and the diaper, after use, cannot be rolled up in a compact style in order to prevent the discharged materials inside the diaper from leaking to the outside. It is therefore an actual situation that the disposable diaper, after use, is fixed or fastened by a tape, a rubber, a string, or the like and then discarded.

Japanese Laid Open Patent Application Nos. Sho 62-69804, Hei 3-176051, etc. propose the techniques in that a tape fastener is provided on each side of the waist portion so that the fastener can be used both for waist adjustment and for fastening of the diaper when the diaper is to be discarded. However, these techniques have such shortcomings that since the tape fasteners are in locations easy for the infant or helper to remove, the fasteners are often removed accidentally, with the result that the diaper is slips down. Moreover, the diaper with such tape fasteners lacks the shorts-like outer appearance.

Furthermore, the tape fasteners thus provided are incapable of effectively preventing the diaper from slipping down because the waist portion is greatly deformed due to busy actions of the wearer.

SUMMARY OF THE INVENTION

It is therefore a first object of the present invention to provide a shorts type disposable diaper which is easy in handling for discard, satisfactory in a sanitary respect at the time the diaper is treated for discard, and does not lose the shorts-like outer appearance when the diaper is worn.

A second object of the present invention is to provide a shorts type disposable diaper in which the wearer is not compelled to keep an unnatural attitude when the wearer is helped to wear the diaper, which can easily be placed on the wearer in the natural attitude (i.e, standing, lying or even fluttering the legs), and in which it is easy to adjust the measurement of the waist portion to fit well to the wearers of all sizes, so that a downward displacement can be prevented, discharged materials inside the diaper do not leak, the condition of discharged materials inside the diaper can easily be seen from outside, and discharged materials can easily be confined in the diaper which is rolled up and fastened by a tape fastener when the diaper is to be discarded.

The present invention has achieved the above-mentioned first object by providing a disposable diaper of the shorts type including a liquid permeable top-sheet, a liquid impermeable backsheet, and an absorber interposed between the topsheet and the backsheet, front and rear waist portions being connected together at opposite sides thereof, respectively, the improvement further including a tape fastener adapted to fasten the diaper when the diaper is to be discarded, the tape fastener being disposed at a central section of an outer surface of the backsheet extending in a longitudinal direction of the backsheet.

Also, the present invention has achieved the above-mentioned first object by providing a disposable diaper of the shorts type including a liquid permeable topsheet, a liquid impermeable backsheet, and an absorber interposed between the topsheet and the backsheet, front and rear waist portions being connected together at opposite sides thereof, respectively, the improvement further including a strip-shaped tape fastener adapted to fasten the diaper when the diaper is to be discarded, the tape fastener being secured at one end thereof to an outer surface of the backsheet or topsheet and directed in a longitudinal direction of the diaper.

Furthermore, the present invention has achieved the above-mentioned second object by providing a disposable diaper of the shorts type including a liquid permeable topsheet, a liquid impermeable backsheet, and an absorber interposed between the topsheet and the backsheet, front and rear waist portions being connected together at opposite sides thereof, respectively, thereby forming a waist opening portion and a pair of leg opening portions, the improvement further including an elastically expansible member disposed at a waist portion in an intermediate area of the diaper between the waist opening portion and the pair of leg opening portions, the expansible member being expanded and contracted in the width direction of the absorber to form a gather about the waist portion, and a tape fastener disposed on an outer surface of the backsheet, the tape fastener having a handle portion directed in a direction parallel to the elastically expansible member.

After use, the disposable diaper of the present invention is rolled up in the longitudinal direction and fastened for discard. Moreover, since the discharged materials can be confined in the diaper thus rolled up and covered with the backsheet, it can be handled in a sanitary manner.

The disposable diaper of the present invention is used in such a manner that the wearer is guided to put the legs into the leg opening portions through the waist opening portion. Once the diaper is placed on the wearer, the diaper fits well to the wearer due to the provision of both the elastically expansible member arranged around a body portion of the diaper and the tape fastener and is prevented from slipping down while in use. Also, due to a provision of the elastically expansible member, the condition of the discharged materials inside the diaper can be seen from outside by eyes without tearing the diaper, for example. After use, the diaper is rolled up in the longitudinal direction and fastened by the tape fastener for discard. In this way, the disposable diaper of the present invention is easy to handle for discard. Moreover, since the diaper, which has been rolled up to confine the discharged materials, can be covered with the backsheet, the diaper for discard can be handled in a sanitary manner.

As seen, the disposable diaper of the present invention is easy to handle for discard and can fully satisfy the requirement from a sanitary aspect at the time the diaper is to be discarded. This can be achieved without sacrificing the normal outer appearance of the diaper in use.

Accordingly, the disposable diaper of the present invention is rolled up, after use, to fully confine the discharged materials, and then fastened by the tape fastener so as to be simply discarded.

The disposable diaper of the present invention can easily be put on the wearer in the natural attitude (standing or lying, or even fluttering the legs) without compelling the wearer to keep an unnatural attitude. Moreover, since the adjustment in measurement about the waist portion is easy, the diaper fits well to the wearers of all sizes and is prevented from slipping down, and the discharged materials in the diaper do not leak to the outside. The condition of the discharged materials in the diaper can easily be seen from outside by eyes. In addition, the discharged materials can easily be confined in the diaper rolled up and then, the diaper is simply discarded after being fastened by the tape fastener.

DETAILED DESCRIPTION OF THE EMBODIMENT

A disposable diaper according to a first embodiment of the present invention will be described with reference to the accompanying drawings.

Figure 1A:
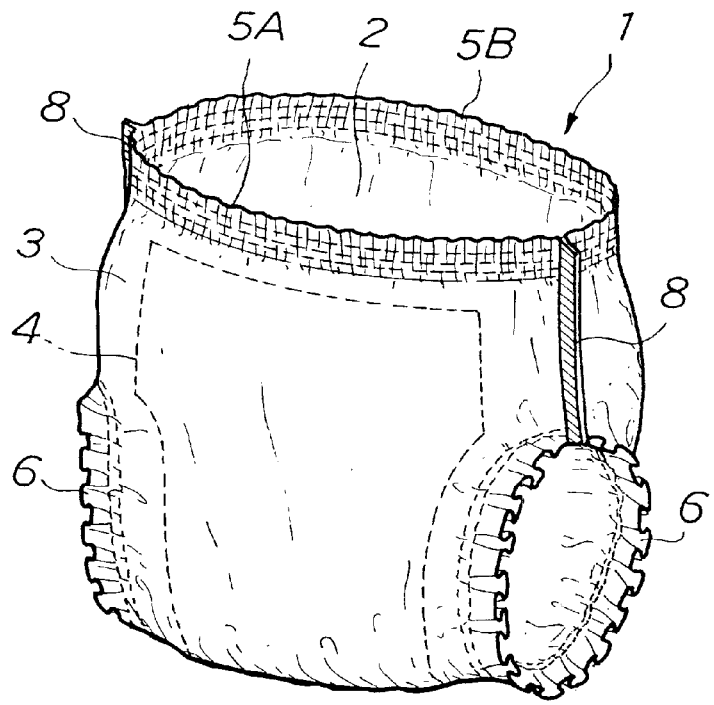
FIG. 1A is a perspective view showing a front side (stomach side) of a disposable diaper according to a first embodiment of the present invention.
Figure 1B:
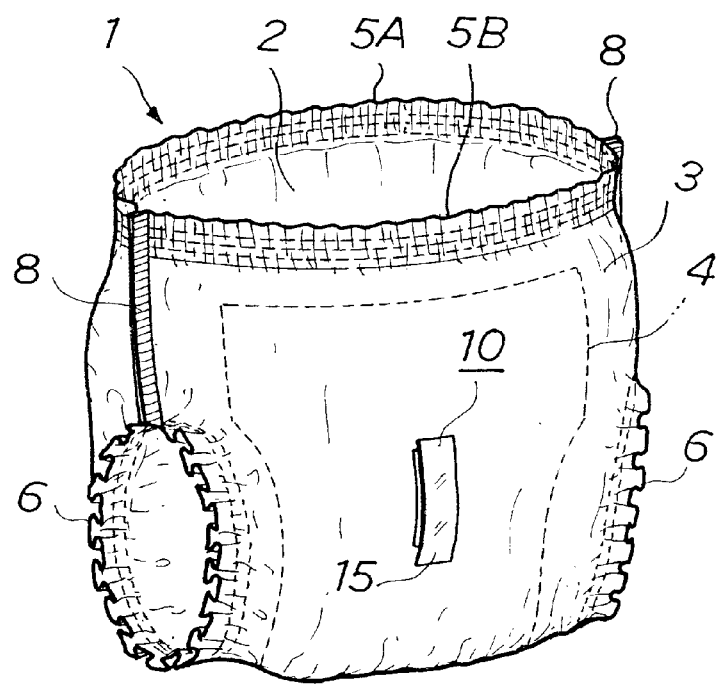
FIG. 1B is a perspective view showing a rear side (back side) thereof.
Figure 2:
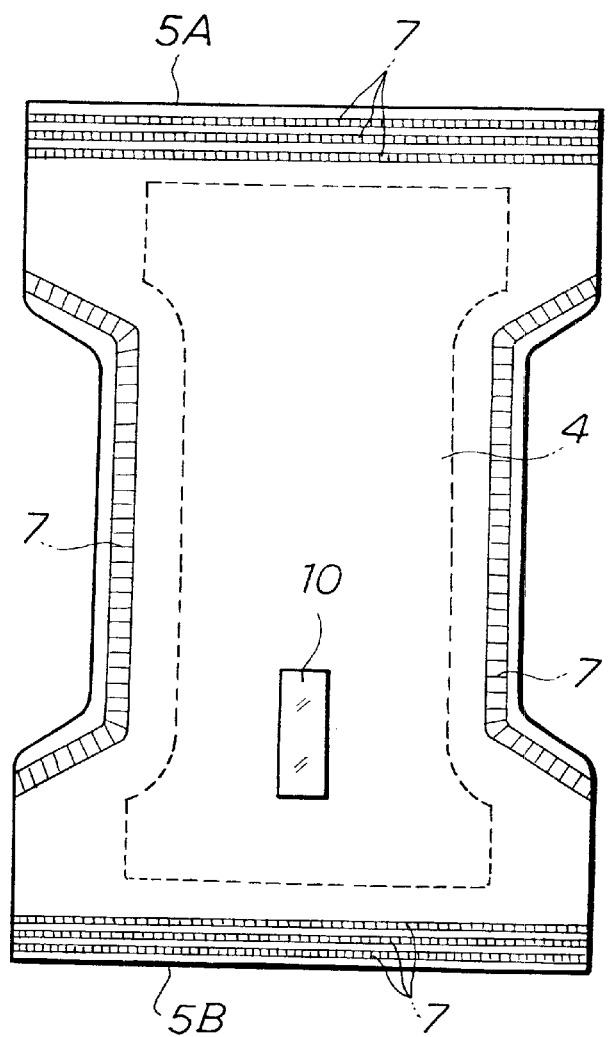
FIG. 2 is a development view of the disposable diaper of FIG. 1.
Figure 3A:
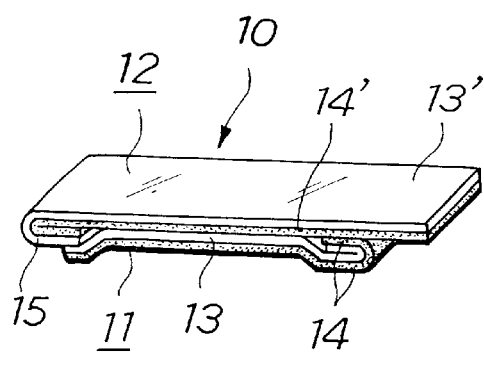
FIG. 3A is an enlarged perspective view of a tape fastener for the use of the disposable diaper of FIG. 1.
Figure 3B:
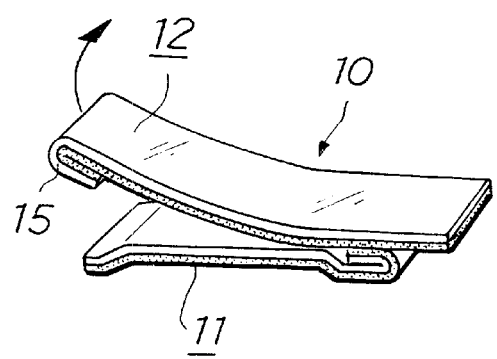
FIG. 3B is an enlarged perspective view of the tape fastener of FIG. 3A in a peeling off condition.

FIG. 1A is a perspective view showing a front side (stomach side) of a disposable diaper according to a first embodiment of the present invention, FIG. 1B is a perspective view showing a rear side (back side) thereof, and FIG. 2. is a development view of the disposable diaper of FIG. 2. FIG. 3A is an enlarged perspective view of a tape fastener in the disposable diaper of FIG. 1, and FIG. 3B is an enlarged perspective view showing a peeling off condition thereof.

As shown in FIGS. 1A and 1B, a disposable diaper 1 of this embodiment is of a shorts type disposable diaper including a liquid permeable topsheet 2, a liquid impermeable backsheet 3, and an absorber 4 interposed between the topsheet 2 and the backsheet 3, front and rear waist portions 5A and 5B being connected together at opposite sides thereof. A tape fastener 10, which is used to fasten the disposable diaper 1 when the diaper is to be discarded, is disposed at a central portion extending in a longitudinal direction of the front surface of the backsheet 3.

More specifically, as shown in FIGS. 1 and 2, in the disposable diaper 1 of this embodiment, the absorber 4 is curved to take the form of a sandglass with an undercrotch portion twisted. Also, the topsheet 2 and the backsheet 3 are curved like the shape of the absorber 4 at the undercrotch portion. The absorber 4 is fixedly sandwiched between the topsheet 2 and the backsheet 3. Elastic members 7 for securely fitting the waist portions 5A and 5B and the leg portions 6 to the diaper wearer when the diaper is worn, are fixed to the front and rear waist portions 5A and 5B at a peripheral edge portion of the absorber 4 by the topsheet 2 and backsheet 3. As shown in FIGS. 1A and 1B, the front waist portion 5A and rear waist portion 5B are connected together at opposite sides thereof, thereby to form connection areas 8. With the foregoing arrangement, the disposable diaper 1 forms the shorts-like shape.

Desirably, the connection areas 8 are easily torn off in the vertical direction. Because, with this arrangement, the diaper can easily be torn off at the connection areas 8 for removal and discarded without making the wearer's skin dirty. The connection areas 8 can be formed by connecting the front waist portion 5A with the rear waist portion 5B at opposite sides thereof by using, for example, a material which can be connected by a hot melt adhesive or supersonic wave and which is preferably soft feeling to the wearer's skin even after connection.

The topsheet 2 is preferably a liquid permeable sheet which is capable of permeating discharged materials into the absorber and which has a feel resembling an undergarment. An acceptable liquid permeable sheet includes, for example, woven fabric, nonwoven fabric, perforated film, or the like. The peripheral edge of the topsheet 2 is subjected to water repellent treatment by applying a hydrophobic compound such as silicon oil or paraffin wave to the peripheral edge, or by preliminarily applying a hydrophilic compound such as alkylic phosphilic ester to its entirety and then washing the peripheral edge with a hot water. By doing this, leakage of urine, etc. permeating the peripheral edge can be prevented.

The backsheet 3 is preferably a moisture permeable, liquid impermeable sheet which is made by adding a thermoplastic resin with a filler and stretched and which is capable of permeating vapor, and preferably has a feel resembling undergarments. An acceptable liquid impermeable sheet includes a composite material composed of a film and a nonwoven fabric, for example.

The absorber 4 is preferably a high absorption polymer chiefly composed of a comminuted pulp or fibrillated pulp, and also preferably a mixture of a thermoplastic resin, a cellulosic fiber and a high absorption polymer which are subjected to heat treatment. The high absorption polymer may be present in any of the upper layer, intermediate layer and lower layer of the absorber 4, and may also be a mixture with a pulp. The high absorption polymer is preferably in a granular state having a water absorption ability capable of absorbing and holding liquid more than twenty times its dead weight and gelled when it absorbs water. Such a high absorption polymer preferably includes a starch-acrylic acid (salt) graft copolymer, a saponified starch-acrylonitrile copolymer, crosslinked polymer of sodium calboxymethyl-cellulose, acrylic acid (salt) polymer or the like.

The elastic member 7 is preferably a yarn rubber, a flat rubber, a film type rubber, or a film-like foamed polyurethane, and also preferably 70 grams (g) to 100 g in stress when stretched 150%. The elastic member 7 is preferably formed from a non-woven type material having expansibility and breathability.

As shown in FIG. 1B, the disposable diaper of this embodiment is provided with a tape fastener 10 disposed at a central section (width-wise central portion of the diaper) of the outer surface of the backsheet 3 extending in the longitudinal direction and adapted to fasten the diaper when the diaper is to be discarded.

The tape fastener 10 of this embodiment will be described in detail. As shown in FIG. 3A, the tape fastener 10 comprises a fixing portion 11 which is to be fixedly connected to the backsheet 3, and an adhering portion 12 for fastening the rolled-up diaper 1 when the diaper 1 is to be discarded. The fixing portion 11 and the adhering portion 12 respectively comprise mounts 13 and 13', and adhesive layers 14 and 14' which are formed by applying an adhesive agent on one surfaces of the mounts 13 and 13'. The outer surface of the mount 13, which contacts the adhesive layer 14' is subjected to peeling treatment.

One end of the fixing portion 11 is bent or folded toward the mount 13 side, while one end of the adhering portion 12 is bent or folded toward the adhesive layer 14' side. The adhesive layer 14 on that portion of the fixing portion 11 which is bent or folded, is in contact with the adhesive layer 14' on the adhering portion 12, thereby affixing the fixing portion 11 and the adhering portion 14. The adhesive layer 14' on the adhering portion 12 and that surface of the mount 13 for the fixing portion 11 which is subjected to the peeling treatment are in contact with each other such that they can be freely adhered and peeled off. An upper end portion of the adhering portion 12 is in contact with the top of the mount 13 at the other end portion of the adhering portion 12 to define a handle 15. As shown in FIG. 3B, the adhering portion 12 can be peeled off the fixing portion 11 by pulling the handle 15 upwardly in a direction as indicated by an arrow.

A material for forming the mounts 13 and 13' is preferably a film, paper, a nonwoven fabric, or a composite material of a film, paper or nonwoven fabric. It is particularly preferable that the mount 13' for the adhering portion 12 is formed from the same material as the backsheet 3. Owing to this arrangement, the outer surface of the tape fastener 10 looks similar to that of the diaper and therefore, the tape fastener can be made less conspicuous, thereby providing a good outer appearance of the diaper. In this case, the mount 13 for the fixing portion 11 may be formed of a different material from the mount 13' for the adhering portion 12.

As the adhesive agent forming the adhesive layers 14 and 14', the same materials as those used for a tape fastener of a normal disposable diaper may be used. For example, there can be listed the styrene block polymer including a styrene-ethylene-butylene-styrene block copolymer (SEBS), a style-isoprene-styrene block copolymer (SIS), a styrene-butadiene-styrene copolymer (SBS), etc. Also, the adhesive agent may be chiefly composed of a natural rubber, a butadien, an acrylic ester or the like.

The above-mentioned peeling treatment is made in accordance with a normal method known in the art.

In order to fixedly connect the tape fastener 10 to the disposable diaper 1, the adhesive layer 14 of the fixing portion 11 of the tape fastener 10 is adhered to the central section of the outer surface of the backsheet 3 in such a manner to direct in the direction as shown in FIG. 1B.

Figure 4:
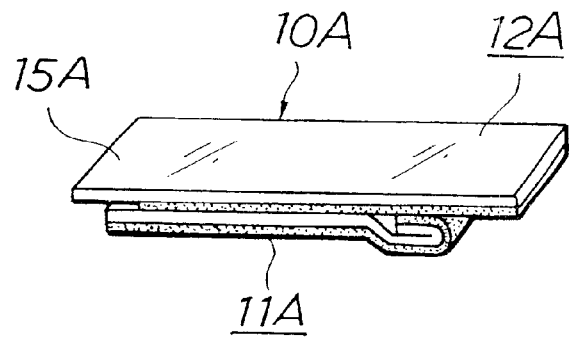
FIG. 4 is an enlarged perspective view showing another example of a tape fastener for the use of the disposable diaper of the present invention.
Figure 5:
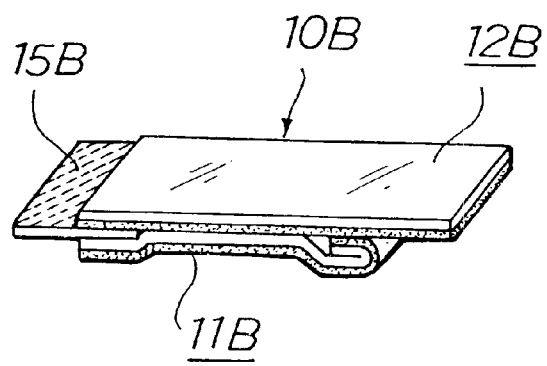
FIG. 5 is an enlarged perspective view showing a further example of a tape fastener for use in the disposable diaper of the present invention.
Figure 6:
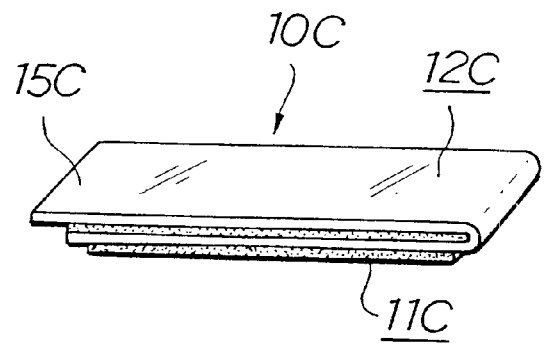
FIG. 6 is an enlarged perspective view showing a still further example of a tape fastener for use in the disposable diaper of the present invention.

Other examples of the tape fastener of the present invention are shown, for example, in FIGS. 4 to 6. FIGS. 4 to 6 are enlarged perspective views showing other examples of the tape fastener used for the disposable diaper of the present invention. Those parts of the tape fasteners of FIGS. 4 to 6 which are not particularly described, are formed in the same manner as the above-mentioned tape fastener 10.

The tape fastener 10A of FIG. 4 has a handle 15A which is formed by providing a portion having no adhesive layer on the adhering portion 12A.

The tape fastener 10B of FIG. 5 has a handle 15B which is formed by adhering a different member to one end of the adhering portion 12B.

The tape fastener 10C of FIG. 6 has a fixing portion 11C and an adhering portion 12C formed by folding an integral mount 13, and a handle 15C formed by providing a portion having no adhesive agent on one end portion of the adhering portion 12C.

The tape fastener used in the present invention may be formed of a Velcro-tape (registered trademark) comprising a male support body and a female support body each including an engagement member can be caught so that they can be mutually caught or engaged. In this case, it is necessary to provide an additional female (male) support body on that area of the diaper corresponding to the tape fastener when the diaper is rolled up, so that the female (male) support body can be engaged with the support body (male or female) of the tape fastener. In case the outer layer of the backsheet 3 is a nonwoven fabric, the tape fastener may be formed only by the male.

Figure 7A:
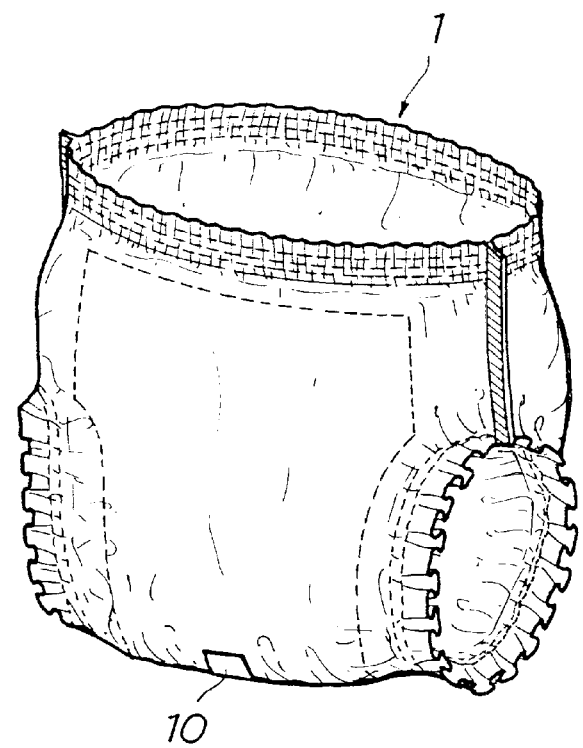
FIG. 7A is a perspective view showing a front side of a disposable diaper according to another embodiment (second embodiment) of the present invention.
Figure 7B:
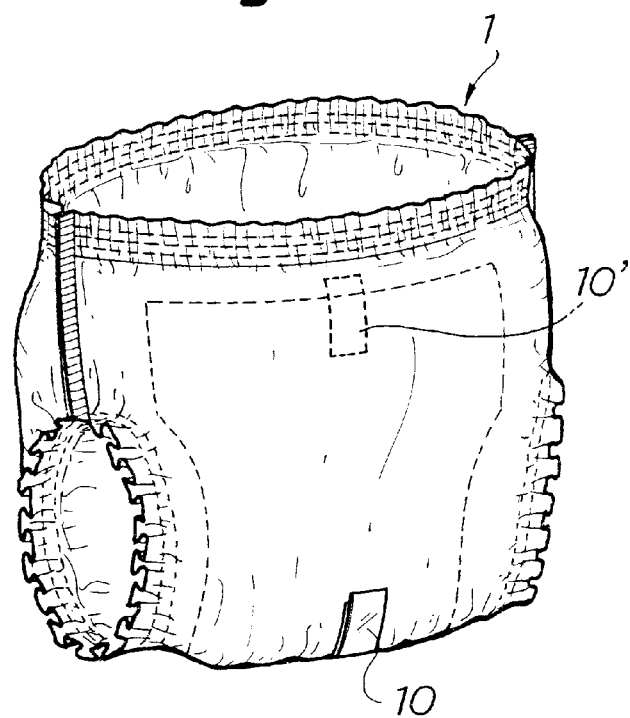
FIG. 7B is a perspective view showing a rear side thereof.

Another example (second embodiment) of a disposable diaper of the present invention is shown in FIG. 7. FIG. 7A is a perspective view showing the front side of the disposable diaper according to the second embodiment of the present invention, and FIG. 7B is a perspective view showing a rear side thereof.

A disposable diaper 1 of FIGS. 7A and 7B has a tape fastener 10 which is disposed at an undercrotch area of the disposable diaper 1. Owing to a provision of the tape fastener 10 at the undercrotch area of the disposable diaper 1, the tape fastener 10 is hidden by a twisting part of the undercrotch portion and therefore, the outer appearance of the diaper can be improved (in other words, it can be made equivalent to the outer appearance of the conventional disposable diaper which is not provided with any tape fastener).

In the above disposable diaper 1, a tape fastener 10' may be provided at the waist portion of the diaper or at an area in the vicinity of the waist portion, as shown by a dotted line of FIG. 7B. Because of this arrangement, the length of the tape fastener can be minimized.

The description made with respect to the first embodiment is likewise applicable to those points of the second embodiment which are not particularly described in detail.

Figure 8A:
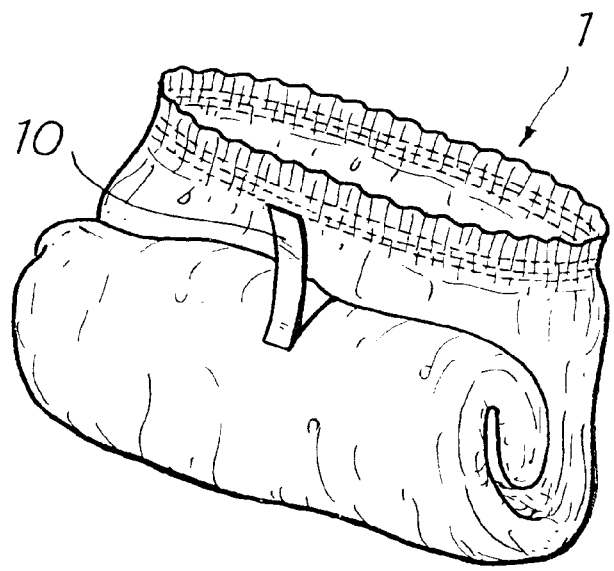
FIG. 8A is a schematic perspective view showing a way of rolling up the disposable diaper of FIG. 1 when the diaper is to be discarded.

Since the disposable diaper 1 of this embodiment is constructed in the manner as mentioned above, it exhibits an excellent discardability after the diaper has been used, as will be described hereinafter in detail with reference to FIGS. 8A and 8B. FIG. 8A is a schematic perspective view showing a way of rolling up the disposable diaper of FIG. 1 when the diaper is to be discarded, and FIG. 8B is a schematic perspective view showing a way of fastening the rolled-up disposable diaper by a tape fastener.

The disposable diaper 1 is used in the same manner as this kind of shorts type disposable diapers. As shown in FIG. 8A, after use, the diaper 1 is rolled up in the longitudinal direction and the adhering portion 12 of the tape fastener 10 is peeled off the fixing portion 11. Thereafter, as shown in FIG. 8B, the disposable diaper 1 is firmly held in the rolled-up condition by the adhesive layer 14' of the adhering portion 12 adhered to the front and rear waist portions 5A and 5B or the like, so that the diaper 1 can easily be discarded in a sanitary manner.

Figure 8B:
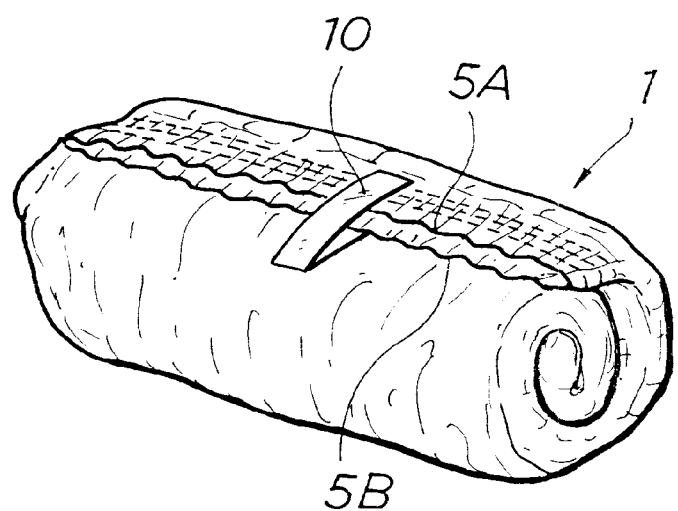
FIG. 8B is a schematic perspective view showing a way of fastening the rolled-up disposable diaper by a tape fastener.

The disposable diaper according to the second embodiment of FIGS. 7A and 7B can also be handled for discard in the same manner as just mentioned.

in FIGS. 8A and 8B, there is shown a method of discard in which the diaper is rolled up first with the undercrotch portion. However, the disposable diaper of the present invention is not limited to this method but can be handled for discard in a variety of methods. For example, the disposable diaper may be rolled up first with the waist portion and the undercrotch portion is fastened by the tape fastener.

Next, a disposable diaper according to a third embodiment of the present invention will be described.

Here, the description made with respect to the first embodiment is likewise applicable to those points of the third embodiment which are not particularly described in detail (for example, material of each component member).

Figure 9:
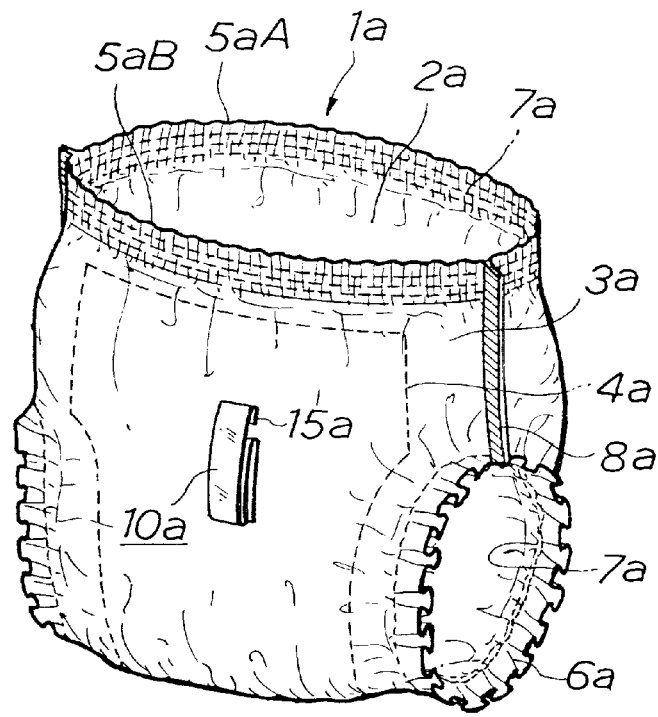
FIG. 9 is a perspective view showing a rear side (back side) of a disposable diaper according to a third embodiment of the present invention.
Figure 10A:
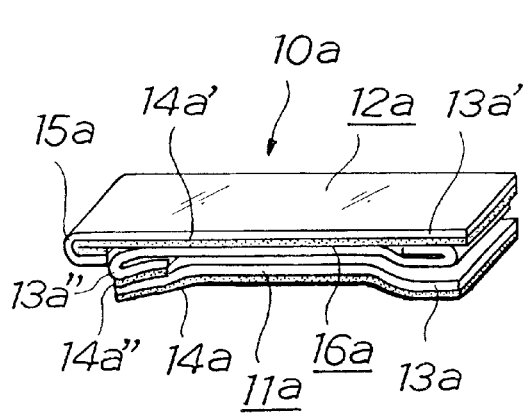
FIG. 10A is an enlarge perspective view of a tape fastener for the use of the disposable diaper of FIG. 9.
Figure 10B:
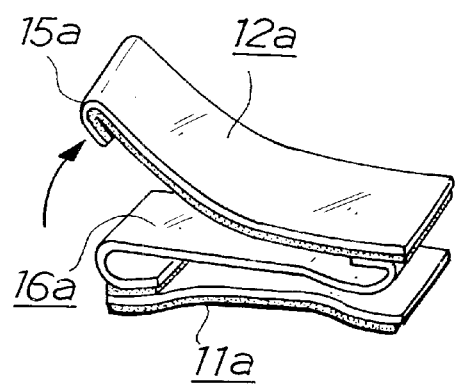
FIG. 10B is an enlarged perspective view of the tape fastener of FIG. 10A in a peeling off condition.

FIG. 9 is a perspective view showing a rear side (back side) of a disposable diaper according to the third embodiment of the present invention. FIG. 10A is an enlarged perspective view of a tape fastener for the use of the disposable diaper of FIG. 9, and FIG. 10B is an enlarged perspective view showing a peeling off condition thereof.

As shown in FIG. 9, the disposable diaper 1a of this embodiment includes a liquid permeable topsheet 2a, a liquid impermeable backsheet 3a, and an absorber 4a interposed between the topsheet 2a and the backsheet 3a. The front and rear waist portions 5aA and 5aB are connected together at opposite sides thereof, respectively. A tape fastener 10a for fastening the diaper when the diaper is to be discarded is disposed on an outer surface of the backsheet 3a and directed in a longitudinal direction of the diaper 1a. One longitudinal end of the tape fastener 10a is secured on the outer surface of the backsheet 3a.

As shown in FIG. 9, the diaper 1a of this embodiment has a strip-shaped tape fastener for fastening the diaper when the diaper is to be discarded, the tape fastener being secured at one end thereof to a central area (width-wise central portion of the diaper) of an outer surface of the backsheet 3a and directed in a longitudinal direction (vertical direction) of the diaper. The taper fastener 10a is folded into three in the longitudinal direction. By doing this, the tape fastener 10a can be stretched in use.

The term "one end" mentioned above refers to one end of the tape fastener and a size thereof is not particularly limited.

The tape fastener 10a of this embodiment will be described in more detail. As shown in FIG. 10A, the tape fastener 10a comprises a fixing portion 11a (serving as the above-mentioned one end) which is to be fixedly connected to the backsheet 3a, an adhering portion 12a for fastening the rolled-up diaper 1a when the diaper 1a is to be discarded, and an intermediate portion 16a for connecting the fixing portion 11a and the adhering portion 12a together. The fixing portion 11a and the adhering portion 12a respectively comprise mounts 13a and 13a', and adhesive layers 14a and 14a' which are formed by applying an adhesive agent on one surfaces of the mounts 13a and 13a'. The intermediate portion 16a comprises a mount 13a", and an adhesive layer 14a" which is formed by applying an adhesive agent to one end portion of the mount 13a".

The intermediate portion 16a is formed into an S-shape by properly folding opposite ends thereof. That end of the intermediate portion 16a which is folded toward the fixing portion 11a side, is provided with the adhesive layer 14a". The adhesive layer 14a" is in contact with one end of the fixing portion 11a, while the mount 13a" for that end of the intermediate portion 16a which is folded toward the adhering portion 12a side is in contact with the adhesive portion 14a" at one end of the adhering portion 12a. Because this arrangement, the fixing portion 11a and the adhering portion 12a are connected together through the intermediate portion 16a, thereby offering the same condition as the tape fastener 10a is folded into three.

The mount 13a in contact with the adhesive layer 14a is subjected to peeling treatment so that it can easily be peeled off when in use.

With respect to the materials for forming the mounts 13a, 13a' and 13a" and the adhesive layers 14a, 14a' and 14a", the description made with respect to the first embodiment is likewise applicable.

The other end portion of the adhering portion 12a is folded toward the adhesive layer 14a' side of the adhering portion 12a to define the handle 15a. As shown in FIG. 10B, by pulling up the handle 15a in the direction as shown by an arrow, the adhering portion 12a can be peeled off the intermediate portion 16a.

Figure 11:
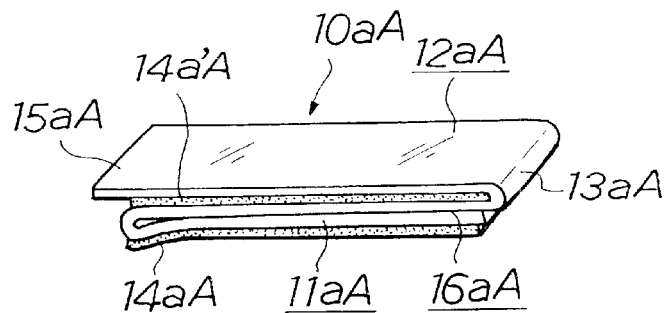
FIG. 11 is an enlarged perspective view showing another example of a tape fastener in the disposable diaper of the present invention.
Figure 12:
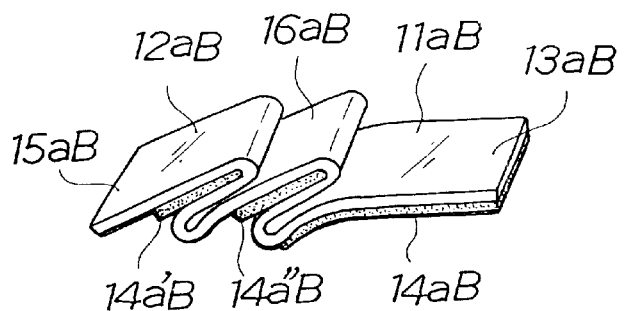
FIG. 12 is an enlarged perspective view showing a further example of a tape fastener in the disposable diaper of the present invention.

As another example of a tape fastener of the present invention, there can be listed a tape fastener which has the construction as shown in FIGS. 11 and 12, for example. Here, FIGS. 11 and 12 are enlarged perspective views showing another example of a tape fastener for use on a disposable diaper according to the present invention. With respect to those points which are not particularly described, the tape fastener of FIGS. 11 and 12 are formed in the same manner as the above-mentioned tape fastener 10.

The tape fastener 10aA of FIG. 11 comprises a strip-shaped mount 13aA having an adhesive area and a peelable area formed on one surface thereof, the adhesive area and the peelable area being superimposed so as to contact with each other, and the mount 13aA being folded into three in the longitudinal direction. More specifically, the mount 13aA is folded into three to form a fixing portion 11aA, an adhering portion 12aA and an intermediate portion 16aA. The fixing portion 11aA is provided at a lower surface thereof with an adhesive layer 14aA, while the adhering portion 12aA is provided at a lower surface thereof with an adhesive layer 14a'A. One end portion of the adhering portion 12aA is provided with a portion on which no adhesive agent is applied, so as to form the handle 15aA.

A tape fastener 10aB of FIG. 12 comprises a strip-shaped mount 13aB having an adhesive area and a peelable area formed on one surface thereof, the adhesive area and the peelable area being superimposed so as to contact with each other, and the mount 13aB being folded into three in the longitudinal direction. More specifically, the mount 13aB has at a lower surface thereof adhesive areas which are respectively provided with adhesive layers 14aB, 14a'B and 14a"B, and peelable areas adjacent to the adhesive areas 14aB, 14a'B and 14a"B and subjected to peeling treatment.

The mount 13aB is folded in the longitudinal direction of the tape fastener such that the adhesive layers 14aB, 14a'B and 14a"B are respectively in contact with the peelable areas, thereby forming the fixing portion 11aB, the adhering portion 12aB and the intermediate portion 16aB.

As the tape fastener for the use of a disposable diaper of the present invention, there can be used a tape rolled up in the longitudinal direction, the mount of the tape being provided at a lower surface thereof with an adhesive layer and an upper surface of the mount being subjected to peeling treatment. Also, the tape consisting the tape fastener may be formed of an elastic member.

Furthermore, in the above-mentioned tape fastener, instead of the peeling treatment applied to the mount, it may be arranged such that a peelable sheet of paper is laid on the outer surface of the backsheet and the adhesive layer is in contact therewith. Also, the peeling treatment may be omitted by providing adhesive layers comprising two kinds of adhesive agents, which can be peeled off between the layers.

As mentioned above, although various forms of tape fasteners can be used in the present invention, it is preferable in view of a good appearance of the diaper that the outer surface of the tape fastener is formed of the same material as the backsheet in any form of the tape fasteners.

Also, in the disposable diaper of the present invention, various forms of the tape fasteners can be provided on the outer surface of the topsheet. In this case, the tape fastener is preferably provided at that part of the diaper (for example, back side of the waist portion, etc.) where the wearer's skin is difficult to get a trace of a contacting mark even if the tape fastener contacts the wearer's skin.

Since the disposable diaper 1a of this embodiment is constructed in the manner as mentioned above, discardability after use is excellent as will be described hereinafter with reference to FIGS. 13A and 13B. Here, FIG. 13A is a schematic perspective view showing the way of rolling up the disposable diaper when the diaper of FIG. 9 is to be discarded, and FIG. 13B is a schematic perspective view showing the way of fastening the rolled-up diaper by the tape fastener.

The above-mentioned disposable diaper 1a is used in the same manner as in the case with this kind of shorts type disposable diaper. As shown in FIG. 13A, after use, the diaper is rolled up in the longitudinal direction, the adhering portion 12a of the tape fastener 10a is peeled off the intermediate portion 16a and stretched in the longitudinal direction, and thereafter, as shown in FIG. 13B, the adhesive layer 14a' of the adhering portion 12a is fastened to the backsheet 3a astride the front and rear waist portions 5aA and 5aB, thereby fixing or fastening the diaper in the rolled-up condition. By doing this, the diaper can easily be discarded in a sanitary manner.

Figure 13A:
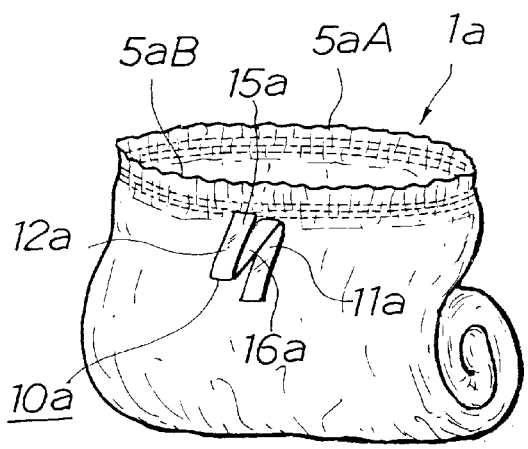
FIG. 13A is a schematic perspective view showing a way of rolling up the disposable diaper of FIG. 9 when the diaper is to be discarded.
Figure 13B:
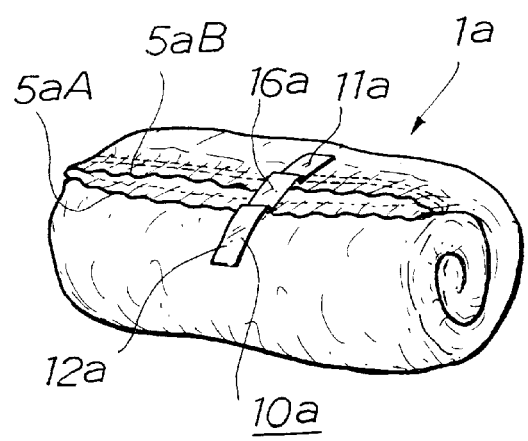
FIG. 13B is a schematic perspective view showing a way of fastening the rolled-up disposable diaper by a tape fastener.

Although FIGS. 13A and 13B show a discarding method in which the diaper is rolled up first with the undercrotch portion, the disposable diaper of the present invention is not limited to this method but many other methods can be employed for discarding the diaper. For example, it is possible that the diaper is rolled up first with the waist portion and the undercrotch portion is fastened by the tape fastener, or the like.

As mentioned above, although it is preferable that the tape fastener for the use of the disposable diaper of the present invention is provided on an upper surface (location in the vicinity of the waist portion of the diaper) of the topsheet or backsheet, the present invention is not limited to this. For example, the tape fastener may be provided at the undercrotch portion of the diaper.

Figure 14:
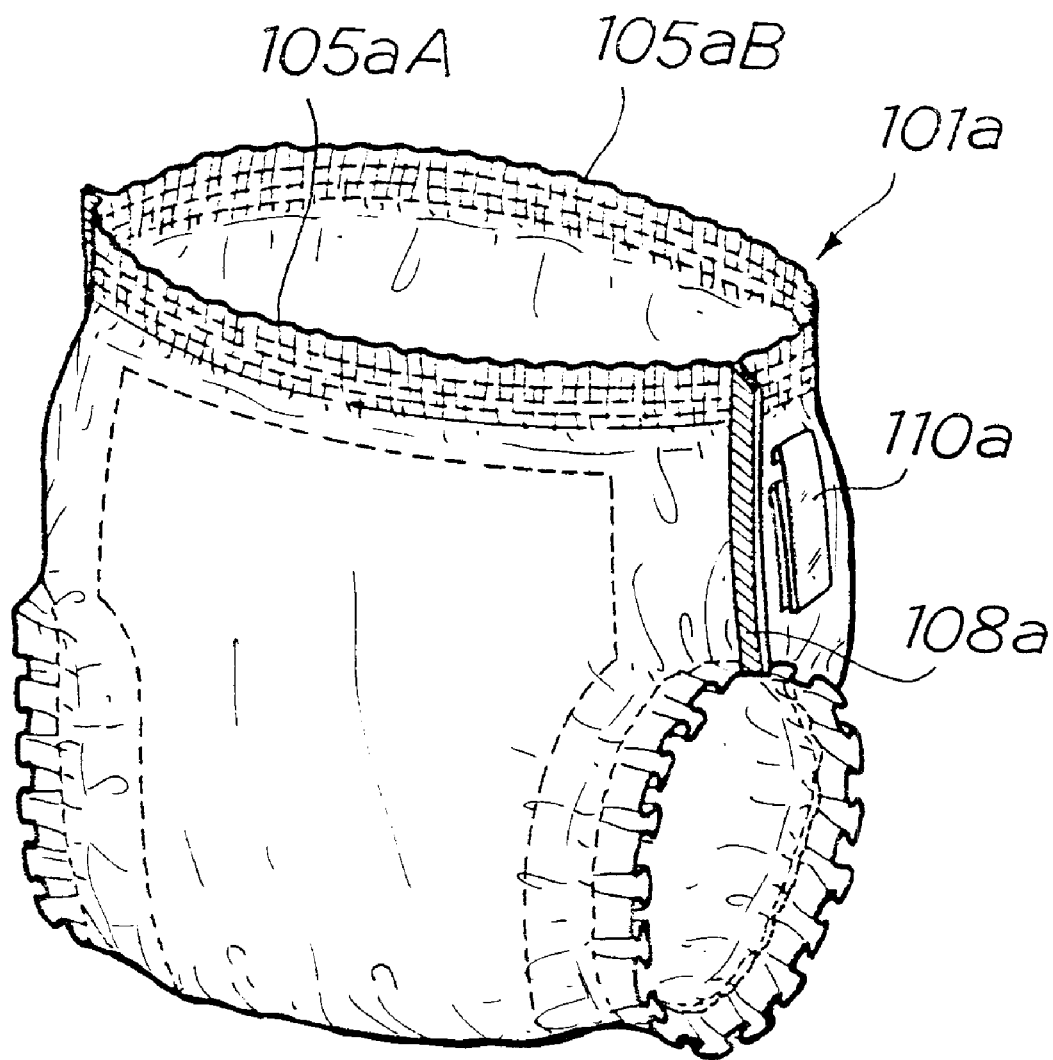
FIG. 14 is a perspective view showing a front side (stomach side) of a disposable diaper according to another embodiment (fourth embodiment) of the present invention.

In the present invention, the tape fastener may be provided at location as shown in FIG. 14, for example. FIG. 14 is a perspective view showing the front side (stomach side) of a disposable diaper according to another embodiment (fourth embodiment) of the present invention. Here, those points which are not particularly described are the same as the disposable diaper 1a of FIG. 9.

In the disposable diaper of FIG. 14, a tape fastener 110a is located adjacent to a connecting portion 108a of the diaper and directed in the longitudinal direction of the disposal diaper with one end thereof fixed.

Next, a disposable diaper according to a fifth embodiment of the present invention will be described in more detail with reference to the accompanying drawings. Here, with respect to the points which are not particularly described in detail, the description made with respect to the first embodiment is applicable.

Figure 15:
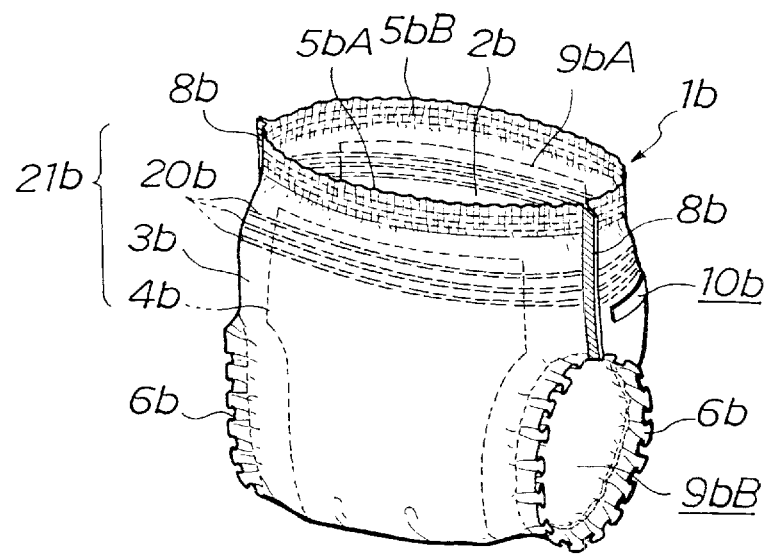
FIG. 15 is a perspective view showing a front side (stomach side) of a disposable diaper according to a fifth embodiment of the present invention.
Figure 16:
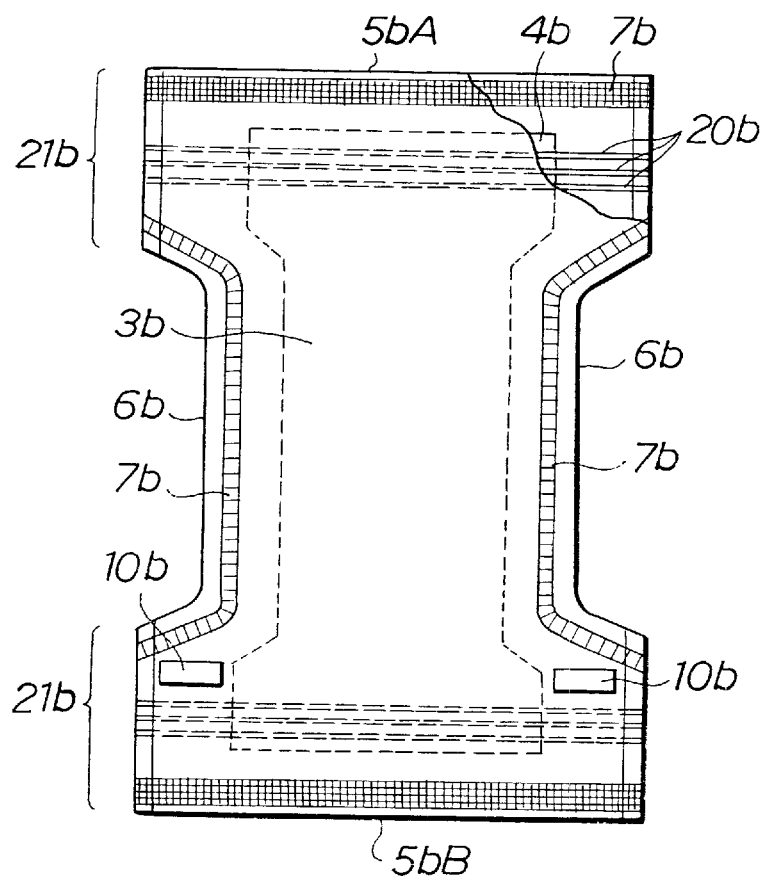
FIG. 16 is a development view of the disposable diaper of FIG. 15.
Figure 17A:
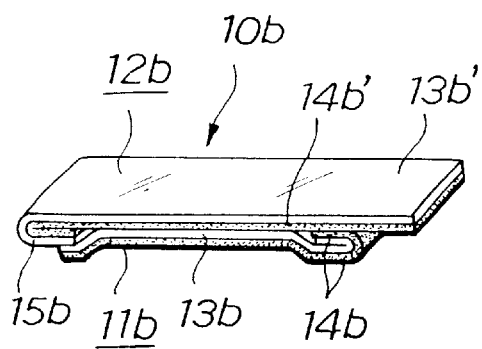
FIG. 17A is an enlarged perspective view of a tape fastener in the disposable diaper of FIG. 15.
Figure 17B:
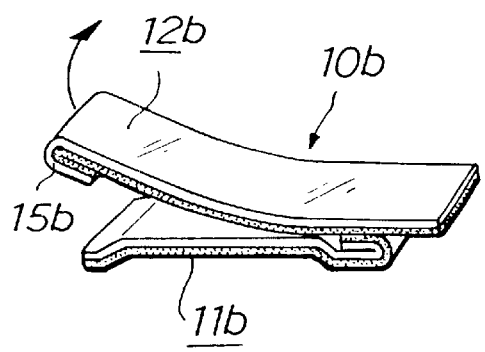
FIG. 17B is an enlarged perspective view of the tape fastener of FIG. 17A in a peeling off condition.

FIG. 15 is a perspective view showing a front side (stomach side) of a disposable diaper according to the fifth embodiment of the present invention, and FIG. 16 is a development view of the disposable diaper of FIG. 15. FIG. 17A is an enlarged perspective view of a tape fastener for the use of the disposable diaper of FIG. 15, and FIG. 17B is an enlarged perspective view showing a peeled-off condition thereof.

As shown in FIG. 15, the disposable diaper 1b of this embodiment includes a liquid permeable topsheet 2b, a liquid impermeable backsheet 3b, and an absorber 4b interposed between the topsheet and the backsheet, front and rear waist portions 5bA and 5bB being connected together at opposite sides thereof, respectively, thereby forming a waist opening portion 9bA and a pair of leg opening portions 9bB. Furthermore, the diaper includes an elastically expansible member 20b disposed at a waist portion 21b in an intermediate area of the diaper between the waist opening portion and the pair of leg opening portions, the expansible member being expanded and contracted in the width direction of the absorber 4b to form a gather about the waist portion 21b, and a tape fastener 10b having a handle portion 15b disposed on an outer surface of the backsheet 3b with the handle portion 15b directing in a parallel direction to the elastically expansible member 20b.

As shown in FIGS. 15 and 16, in the disposable diaper 1b of this embodiment, there is provided an elastically expansible member 20b disposed at a waist portion 21b in an intermediate area of the diaper between the waist opening portion and the pair of leg opening portions, the expansible member being expanded and contracted in the width direction of the absorber 4b to form a gather about the waist portion 21b.

Three of the elastically expansible members 20b are arranged at a generally central portion (in the sense of a vertical direction of the diaper) of the waist portion 21b at predetermined spaces in the vertical direction of the diaper, and fixedly sandwiched between the backsheet 3b and the absorber 4b.

With respect to the material forming the elastically expansible member 20b, the same material forming the above-mentioned elastic member 7b (same as the elastic member 7 described with respect to the first embodiment) can be used.

As shown in FIGS. 15 and 16, in the disposable diaper 1b of this embodiment, the tape fastener 10b having the handle 15b is disposed on the outer surface of the backsheet 3b and beneath (undercrotch direction of the diaper) the elastically expansible member 20b at the back portion of the diaper such that the handle 15b is directed in a direction parallel to the elastically expansible member 20b. In other words, the longitudinal direction of the tape fastener 10b is directed in a direction parallel to the elastically expansible member 20b.

The tape fastener 10b of this embodiment will be described in more detail. As shown in FIG. 17A, the tape fastener 10b comprises a fixing portion 11b fixedly connected to the backsheet 3b, and an adhering portion 12b for adjusting the dimension around the waist portion of the diaper and fastening the rolled-up diaper when the diaper is to be discarded. The fixing portion 11b and the adhering portion 12b respectively comprise mounts 13b and 13b', and adhesive layers 14b and 14b' formed by applying an adhesive agent to one surfaces of the mounts 13b and 13b'. That outer surface of the mount 13b, which is in contact with the adhesive layer 14b', is subjected to peeling treatment. Here, with respect to the materials forming the adhesive layers 14 and 14', the description made with respect to the first embodiment is applicable.

Since the disposable diaper 1b of this embodiment is constructed in the manner as mentioned above, the following effects are obtained.

That is, in the conventional shorts type disposable diaper having no tape fastener, the diaper is fitted to the wearer only by the elastically expansible member disposed at the waist portion. However, in case the length dimension around the waist portion of the disposable diaper is longer than the waist dimension of the wearer, the provision of only the elastically expansible member is not enough and there is a possibility that the diaper will slip down.

However, in the disposable diaper 1b of this embodiment, by properly adjusting the dimension around the waist portion with the tape fastener 10b, the maximum function of the elastically expansible member 7b disposed at the waist portion can be exhibited to improve the fitness.

On the contrary, in the diaper having only the tape fastener as means for fitness, it is difficult for such diaper to follow the change in dimension around the waist portion due to the wearer's activity. The result is that the tightening is too much or the diaper is displaced while in use. However, in the disposable diaper 1b of the present invention, the inconveniences experienced in the conventional diaper are obviated because the elastically expansible member 20b eases the stress applied to the tape fastener 10b.

Also, in the fifth embodiment, aside from the above-mentioned tape fastener 10b, the tape fasteners having the constructions as shown in FIGS. 4 to 6 which are described with reference to the first embodiment, may be used.

Figure 18:
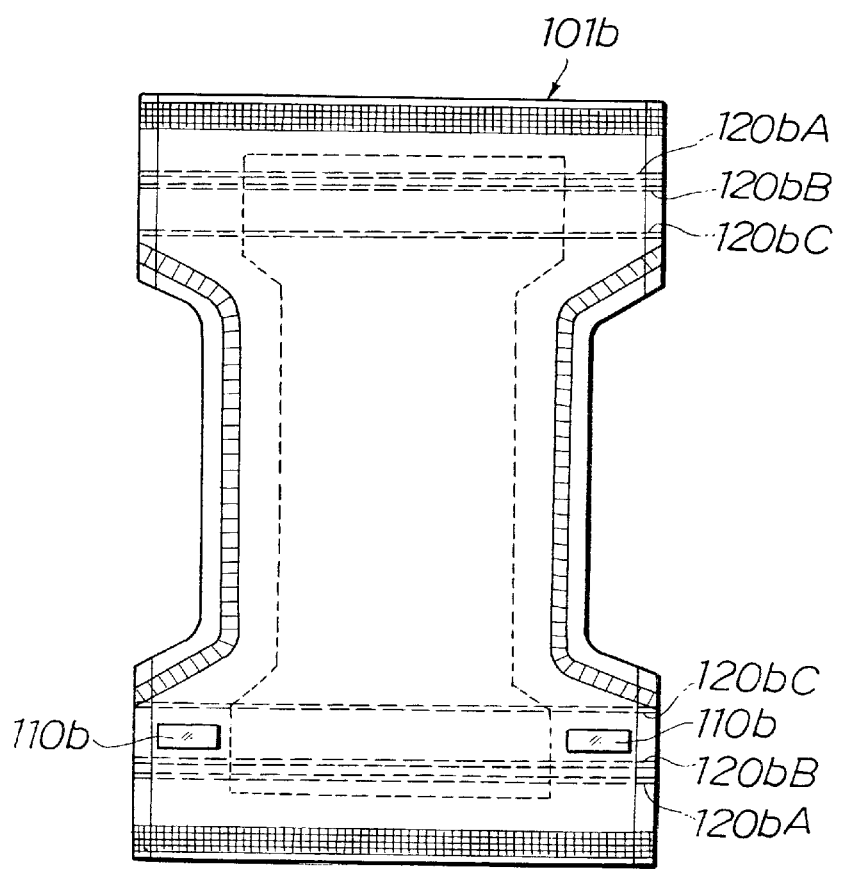
FIG. 18 is a development view of a disposable diaper according to another embodiment (sixth embodiment) of the present invention.
Figure 19:
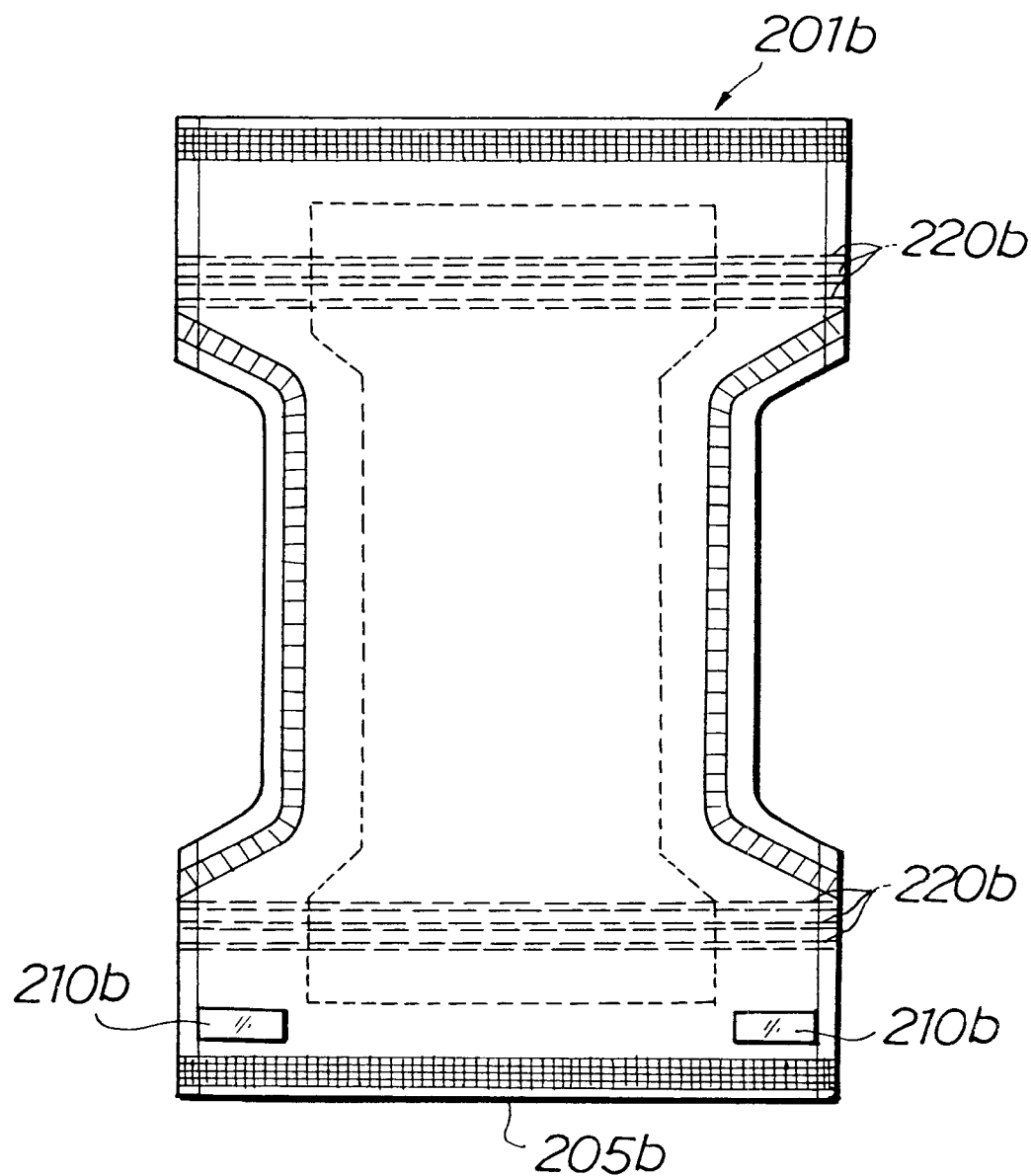
FIG. 19 is a development view of a disposable diaper according to another embodiment (seventh embodiment) of the present invention.

The disposable diaper of the present invention is not limited to the above-mentioned constructions. For example, it can be constructed in the manner as shown in FIGS. 18 and 19. FIG. 18 is a development view of a disposable diaper according to another embodiment (sixth embodiment) of the present invention, and FIG. 19 is a development view of a disposable diaper according to another embodiment (seventh embodiment) of the present invention. With respect to those points which are not particularly described in detail, the description made with respect to the fifth embodiment is applicable.

In a disposable diaper 101b according to another embodiment (sixth embodiment) of the present invention of FIG. 18, tape fasteners 110b (two in the illustrated embodiment) are disposed between elastically expansible members 120bA and 120bB, and an elastically expansible member 120bC. More specifically, the elastically expansible members 120bA and 120bB are arranged at a predetermined space, and the tape fasteners 110b are provided downwardly of the expansible members. The remaining elastically expansible member 120bC is disposed downwardly of the tape fasteners 10b.

In the disposable diaper 201b according to another embodiment (sixth embodiment) of the present invention of FIG. 19, tape fasteners 210b (two in the illustrated embodiment) are disposed upwardly (toward the waist portion 205b of the diaper) of three elastically expansible members 120bA, 120bB, and 120bC which are arranged at predetermined spaces.

In any of the above embodiments, the disposable diaper is provided with three elastically expansible members. However, the present invention is not limited to these embodiments. For example, a single, two, or four or more elastically expansible members may be provided.

The disposable diapers lb according to the embodiments of FIGS. 5 to 7 are used in the same manner as this kind of shorts type disposable diapers, and can be discarded, after use, in the manner as will be described hereinafter.

After the diaper 1b is vertically folded into two, it is width-wise folded into three and then the diaper in a rolled-up condition is fastened by adhering the adhering portion 14b' of the tape fastener 10b thereto.

In this way, the disposable diaper can easily be discarded in a sanitary manner.

The disposable diaper of the present invention can also be discarded in other manners than described above. For example, it is possible that the diaper is rolled up first with the waist portion and the undercrotch portion is fastened by the tape fastener for discard.

What is claimed is:

1. A pull-on disposable shorts diaper comprising:

a front surface area and a rear surface area having opposing lateral side portions which are connected together along continuous seams at the opposing lateral side portions to form shorts having a waist opening and a pair of leg openings, said continuous seams extending from the waist opening to the leg openings, respectively, the rear surface area having a rear waist portion including elastically expansible members, the front surface area having a front waist portion including elastically expansible members, each of the leg openings including elastically expansible members, said front and rear waist portions defining said waist opening;

a liquid permeable topsheet;

a liquid impermeable backsheet;

an absorber interposed between said topsheet and said backsheet;

a strip-shaped tape fastener positioned at a central section of the rear surface area of the shorts diaper, substantially laterally between the opposing side portions and below the elastically expansible members of said rear waist portion, on an outer surface of said backsheet, opposing longitudinal ends of said tape fastener being oriented in a direction parallel to said opposing side portions, with one of said longitudinal ends being a fixed portion that is secured to the outer surface of the shorts diaper, and said tape fastener being vertically folded, and the other longitudinal end being a fastening portion for fastening the shorts diaper upon disposal of said shorts diaper; and said tape fastener being positioned entirely on the rear surface area of said shorts diaper in non-use, and extended and wrapped over said waist opening to form a roll structure upon disposal, whereby said shorts diaper is discarded in a sanitary manner.

2. The pull-on disposable shorts diaper according to claim 1, wherein said tape fastener further comprises an intermediate portion connecting said fixed portion and said fastening portion, said tape fastener being folded in three layers comprising said fixed portion, said intermediate portion and said fastening portion, respectively.

3. The pull-on disposable shorts diaper according to claim 1, wherein said tape fastener includes an adhesive area and a peelable area, said adhesive area and said peelable area being superimposed so as to contact each other when said tape fastener is in a folded condition.

* * * * *